United States Patent
Deuerling-Zheng et al.

(10) Patent No.: US 8,755,583 B2
(45) Date of Patent: Jun. 17, 2014

(54) METHOD AND APPARATUS FOR GENERATING A FUNCTIONAL DATA SET OF A PERFUSED REGION OF THE HUMAN OR ANIMAL BODY

(75) Inventors: Yu Deuerling-Zheng, Erlangen (DE); Thomas Redel, Poxdorf (DE); Michael Zellerhoff, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 776 days.

(21) Appl. No.: 12/729,269

(22) Filed: Mar. 23, 2010

(65) Prior Publication Data

US 2010/0246916 A1 Sep. 30, 2010

(30) Foreign Application Priority Data

Mar. 27, 2009 (DE) .......................... 10 2009 015 386

(51) Int. Cl.
*G01N 23/04* (2006.01)
*G06K 9/00* (2006.01)
*H05G 1/08* (2006.01)

(52) U.S. Cl.
USPC .............................. 382/131; 378/91; 378/62

(58) Field of Classification Search
USPC ......................................................... 382/131
See application file for complete search history.

(56) References Cited

U.S. PATENT DOCUMENTS

| | | | | |
|---|---|---|---|---|
| 6,102,858 A * | 8/2000 | Hatfield et al. | ............... | 600/443 |
| 2004/0101088 A1 | 5/2004 | Sabol et al. | | |
| 2004/0195512 A1 * | 10/2004 | Crosetto | .................. | 250/363.04 |
| 2006/0285738 A1 | 12/2006 | Boese et al. | | |
| 2008/0107233 A1 * | 5/2008 | Sakaguchi et al. | ............. | 378/91 |

FOREIGN PATENT DOCUMENTS

DE 102007024450 A1 11/2008

OTHER PUBLICATIONS

Martin et al., "Assessment of Vasculature of Meningiomas and the Effects of Embolization with Intra-arterial MR Perfusion Imaging: A Feasibility Study", Oct. 2007, pp. 1771-1777. vol. 28, American Journal of Neuroradiology.
Oestergaard, "Principles of cerebral perfusion imaging by bolus tracking", Journal of Magnetic Resonance Imaging, 2005, pp. 710-717, 22(6).

* cited by examiner

*Primary Examiner* — Hiep V Nguyen

(57) ABSTRACT

A method and apparatus for generating at least one functional data set of a perfused region of the human or animal body are proposed. A first image data set is supplied comprising at least two images of the perfused region recorded at different times before and after an injection of contrast agent into a first artery supplying the region. A second image data set is supplied comprising at least two images of the perfused region recorded at different times before and after an injection of contrast agent into a second artery supplying the region. A first functional data set is generated by pixel-based calculation of at least one perfusion parameter from the first image data set. A second functional data set is generated by pixel-based calculation of at least one perfusion parameter from the second image data set.

16 Claims, 2 Drawing Sheets left side superimposition right side

METHOD AND APPARATUS FOR GENERATING A FUNCTIONAL DATA SET OF A PERFUSED REGION OF THE HUMAN OR ANIMAL BODY

CROSS REFERENCE TO RELATED APPLICATIONS

This application claims priority of German application No. 10 2009 015 386.1 filed Mar. 27, 2009, which is incorporated by reference herein in its entirety.

FIELD OF THE INVENTION

The present invention relates to a method and apparatus for generating a functional data set of a perfused region of the human or animal body. The invention also relates to a computer program product, which implements the inventive method.

BACKGROUND OF THE INVENTION

As well as established methods such as computed tomography (CT) and magnetic resonance tomography (MRT), 3D imaging using a C-arm is also available for an imaging diagnosis of cerebral diseases such as a stroke, arteriovenous malfunction or AVM and cancers. All these methods have in common the fact that they supply morphological information relating to the tissue.

The flow of blood through tissue, in other words the perfusion of an organ for example, is a further important functional parameter. By determining a perfusion parameter (blood throughflow parameter) it is possible to identify, locate and determine the extent of a blood throughflow problem. It is possible to use such information, in particular by determining a number of perfusion parameters, to plan an optimum therapy and to check its success by a repeat determination.

Until now imaging methods such as computed tomography (CT) and magnetic resonance tomography (MRT) have been used to determine tissue perfusion. With such methods a contrast agent bolus is injected into a vein and the flow of the contrast agent into the tissue is tracked by imaging. Such a method, also known as bolus tracking, is described for example in the article by Leif Oestergaard, "Principles of cerebral perfusion imaging by bolus tracking", Journal of Magnetic Resonance Imaging. 22(6): 710-717. Such methods however only supply information about the overall perfusion of the tissue, as the contrast agent used to record the image can only be injected into a peripheral vein.

Selective injection of the contrast agent into an artery is not possible while the patient is in an MRT or CT device. This is because the insertion of a catheter into an artery to administer the contrast agent is only possible with image-based guidance, as provided for example by an interventional x-ray device, e.g. an angiography device. The images produced by an MRT or CT device are not suitable for monitoring the insertion of a catheter into an artery. If in practice for example a selective arterial injection of the contrast agent is required, the patient to be treated must be transported between the catheter laboratory and the CT or MRT examination room. This considerable transportation outlay means that in practice only a few vessels can be included in the examination.

Embolization is an example of an important intervention-based method for treating bleeding, vessel malformations or tumors with a large number of blood vessels by occluding the blood vessels. Every effort is made only to close off the affected blood vessels where possible, without endangering the surrounding healthy vessels in the process. One example of a tumor with a large number of blood vessels is a meningioma (brain tumor) and the therapy of choice to treat such a tumor is an operation, in which the blood vessels leading to the tumor are increasingly frequently specifically occluded by means of interventions in preparation for the operation, to minimize blood loss during the operation. However such embolization requires a precise knowledge of the blood vessels supplying the tumor. As well as a simple angiograph it is also very helpful here to measure the perfusion and in particular the blood volume in 3D.

A specific problem that frequently occurs with meningiomas in particular is that such a tumor is supplied by way of various blood vessels. Embolization however has to be highly selective in order to ensure the supply to the brain parenchyma even after embolization. It is therefore essential to determine the supplying blood vessels and the areas of the tumor with blood flowing through carefully before the operation by means of a number of selective or superselective arterial contrast agent injections.

The embolization of meningiomas by means of perfusion imaging was described for example by A. J. Martin, S. Cha, R. T. Higashida, S. P. Cullen, V. Halbach, C. F. Dowd, M. W. McDermott and D. A. Saloner in "Assessment of Vasculature of Meningiomas and the Effects of Embolization with Intra-arterial MR Perfusion Imaging: A Feasibility Study", *AJNR Am. J. Neuroradiol.*, October 2007, 28: 1771-1777. Here Martin et al. describe a method for interventional angiography and catheter placement, combined with a perfusion measurement by means of magnetic resonance (MR). In this process an angiographic system is used to position a catheter by means of an intervention with simultaneous fluoroscopy in a vessel supplying the meningioma (e.g. in the external carotid artery (Arteria carotis externa)). The patient is then transferred to the MRT system and perfusion is measured with a selective contrast agent injection. Perfusion is then measured by means of selective contrast agent injection into a further vessel supplying the tumor. The not very selective carotid artery (Arteria carotis communis) is however selected here. The reason for this restriction is that the catheter can only be moved into this position by simple retraction, as the patient would otherwise have to be moved back into the fluoroscopy system and then be transferred back to MR once the catheter had been repositioned. Patient transportation makes this procedure very cumbersome and the evaluation and interpretation of the results is very complicated, as two true superselective contrast agent injections cannot be carried out.

Generally there is also a need or the necessity for other applications, such as the perfusion of liver tumors, the perfusion of the brain parenchyma after a stroke, etc., to obtain information about the resulting overall perfusion of defined structures based on a number of selective or superselective individual contrast agent injections.

SUMMARY OF THE INVENTION

The object of the present invention is therefore to provide a method, which allows better information to be supplied about the resulting overall perfusion of defined structures, e.g. of tissues such as the liver and brain of humans and animals.

According to the invention this object is achieved by the features of the independent claims. The dependent claims specify preferred embodiments.

According to the invention therefore a first method for generating at least one functional data set of a perfused region of the human or animal body is claimed, having the following steps:

Supplying a first image data set, comprising at least two images of the perfused region, which were recorded at different times before and after an injection of contrast agent into a first artery supplying the region;

Supplying a second image data set, comprising at least two images of the perfused region, which were recorded at different times before and after an injection of contrast agent into a second artery supplying the region;

Generating a first functional data set by pixel-based calculation of at least one perfusion parameter from the first image data set and Generating a second functional data set by pixel-based calculation of at least one perfusion parameter from the second image data set.

The perfused region of the human or animal body is a region in which tissue, which is supplied with blood and is therefore capillarized, is present. The region preferably contains an organ such as the brain or liver, kidney, lung, prostate, pancreas or heart. It can also be a muscle or another human or animal organ.

The invention is based on the knowledge that perfusion measurement after a selective contrast agent injection into two different arteries, which supply the same region of the body, provides particularly informative findings. Because of the problems described above in respect of positioning a catheter in different arteries, such a method has not been known until now. In the cited article by A. J. Martin et al. the second contrast agent injection takes place into the not very selective carotid artery (arteria carotis communis). In the case of the invention however both image data sets are obtained after one selective or superselective injection of contrast agent. The first and second arteries are preferably of approximately the same size or height in the vascular tree. The two arteries for example supply adjacent regions, such as the right and left halves of the brain, or at least approximately the same region.

The method is preferably carried out using images from the first and second image data sets, which were generated using an angiography device, in particular a C-arm x-ray device. An angiography device refers to an x-ray device, which is suitable for interventions. In particular such an angiography device has an x-ray tube and an x-ray detector, which can be moved around the perfused region or as the case may be around a patient.

A C-arm x-ray device refers to an x-ray device, in which the x-ray tube and the x-ray detector are secured to a C-arm that can be rotated about the object.

Such angiography devices have the advantage that the first and second image data sets can be recorded during the same session or intervention, in other words without moving the patient out of the angiography device. Between the recording of the first and second image data sets a catheter, through which the contrast agent required for the functional recordings is injected, is removed from the first artery and moved into the second artery, preferably being advanced in this process, in other words toward smaller arteries in the vascular tree. This process is preferably image-controlled, in other words it takes place as the C-arm records x-ray images (fluoroscopy images) in real time.

Of course the invention can also be used to process more than two image data sets, in particular three or four image data sets, which were all recorded before and after an injection of contrast agent into a further artery supplying the region.

The inventive method is preferably used immediately before, during or for direct control after an intervention on a vessel, e.g. in the case of a stroke. One particularly advantageous application is the separate contrast agent injection into the left and right internal carotid artery (Arteria carotis interna), since this means that essentially only the perfusion of the corresponding hemisphere of the brain is measured. However there is also a flow of blood through the opposite hemisphere by way of the Circulus Willisi (cerebral arterial circle). Conversely the hemisphere to be examined is also supplied with blood, which does not contain contrast agent, by way of the Circulus Willisi, which can falsify the results. Only a combined evaluation by means of two suitably combined selective contrast agent injections into both carotids can supply a result that provides a significant amount of information relating to the perfusion. It is also necessary to take into account the supply to the hemispheres by way of the vertebral arteries or as the case may be the basilar arteries. This would be an example of the use of more than two, in particular four or five, image data sets in the context of the invention.

An image of the perfused region refers to a 2D matrix or 3D matrix containing spatially resolved image data in the form of gray scale values, which correspond to the perfused region displayed. The images are preferably obtained by means of x-ray beams; in particular the 2D images are preferably projection images. A 3D image of the perfused region can also be obtained using a C-arm x-ray device, by means of what is known as a rotational pass. Here the C-arm is moved once through approximately 180° plus fan angle of the x-ray source around the human or animal body, in which process 2D projection images are recorded at short time intervals. For example approximately 50 to 500 projection images are thus acquired within around 1 to 5 seconds. These images can then be used to reconstruct a 3D image volume by means of appropriate back-projection methods (e.g. filtered back-projection).

The first and second image data sets each contain at least two such (2D or 3D) images of the perfused region, of which at least one was recorded before the arrival of the injected contrast agent in the perfused region and at least one after the inflow of contrast agent. Perfusion parameters can be calculated for example from the difference between such images or as the case may be by means of further analysis methods. This is done on a pixel basis, in other words for at least some pixels of the first or second image data set. The perfusion parameters thus calculated are stored pixel by pixel in a functional data set.

A functional data set therefore refers to a 2D or 3D data set, which contains spatially resolved data, which corresponds to at least one perfusion parameter, for example the blood volume (BV), blood flow (BF), time to arrival of the contrast agent (arrival time), time to maximum contrast/fill (time to peak), mean-transit time (MTT) of the contrast agent over time or a parameter proportional to one of these values or composed from these values. The functional data set can also contain data relating to a number of these perfusion parameters, e.g. one value proportional to the blood volume (BV) and one value proportional to the blood flow (BF) for each pixel/voxel.

The functional data set covers for example the same space in the human or animal body as the images of the image data set and has in particular the same dimensions (2D or 3D, with the same number of pixels/voxels).

One aim of the invention is to be able to compare the image data obtained from the first and second image data sets (in other words during injection into different arteries). This can be done in two different ways:

According to the first method a first functional data set is calculated by means of corresponding analysis from the first image data set and a second functional data set from the second image data set. These can either be displayed next to one another and evaluated by this means or they are superimposed on one another. They are preferably linked to form an overall functional data set, for example by addition. This method has the advantage that the first and second overall functional data sets can as a result be displayed and evaluated separately.

According to the second method the first and second image data sets are first linked to form an overall image data set, for example by addition, optionally with prior weighting or normalization. An overall functional data set is then generated from the overall image data set by means of pixel-based calculation of at least one perfusion parameter. For example the overall functional data set has the same dimensions (number of pixels/voxels) as the overall image data set. The overall functional data set preferably represents the overall perfusion of the perfused region.

The first and second image data sets and the images contained therein preferably all cover the same region in the human or animal body. In particular the at least two images in each image data set respectively cover the same region, particularly as they were recorded shortly after one another. It is however possible for the images of the first and second image data sets only to overlap partially, in particular if the first and second arteries each supply regions, which only overlap partially.

The first and second image data sets can contain images according to the four variants described below:

According to a first variant the first and second image data sets each comprise at least one native 2D image and one contrasted 2D image, these preferably being 2D projection images. The contrasted 2D image was preferably recorded with the perfused region filled to the maximum with contrast agent or at least filled approximately to the maximum. A number of contrasted 2D images are preferably recorded one after the other and the one with the greatest contrast, in other words the highest fill level, is selected. The native 2D image is recorded before the contrast agent arrives. To calculate a perfusion parameter, the native 2D image is subtracted from the contrasted 2D image. This gives a value which is proportional to the blood volume, to the cerebral blood volume (CBV) in the case of the brain.

The second variant is like the first but instead of the native and contrasted 2D images a 3D image is used in each instance. This is preferably recorded using the rotational pass described above. Since acquisition therefore takes a few seconds, the contrast agent bolus must be long enough, e.g. five seconds or longer. A corresponding native 3D image is then subtracted from the 3D image, which is reconstructed from the projection images acquired in the rotational pass during the injection. The second variant can also be embodied like the first.

In order to be able to compare the first and second image data sets or the first and second functional data sets obtained therefrom, it is advantageous to normalize the image data set or functional data to the contrast agent concentration. This is preferably done against what is known as the arterial input function (AIF). This can be derived on the one hand from the protocoled injection parameters. In order to determine the AIF as locally as possible, in other words in the vessels supplying the perfused region, a pixel in the contrasted image, which is on the supplying artery, is selected and used for normalization.

In both the first and second variant it is possible to register both the two images of each image data set and the two image data sets themselves with one another, before they are analyzed and linked correspondingly. Registration is a mapping or displacement of one image in relation to another image of the same region, so that corresponding structures within the region are mapped onto one another. Registration preferably takes place using structures, which are present in both the native and the contrasted images, e.g. using bony structures. For example only the native images of the two image data sets are registered with one another in each instance.

According to a third variant the first and second image data sets each comprise a series from consecutively recorded 2D images. These preferably cover at least the period of the first pass, in other words the first flow of the contrast agent through the perfused region. The series comprises for example 10 to 1000 images, each acquired one after the other at time intervals of between 5 ms and 500 ms. The 2D images are preferably x-ray images again, particularly preferably fluoroscopy images generated using a C-arm system. The C-arm is generally not moved during the acquisition of a series, so that all the projection images have been recorded from the same direction. The C-arm is also particularly preferably not moved between the recording of the series of the first and second image data sets. It is however also possible to move the C-arm around the patient between two series, in order to be able to record the associated series from an ideal viewing angle for each supplying artery.

The recording of a series has the advantage that further perfusion parameters can be calculated from the dynamic of the arrival and departure of the contrast agent, e.g. the blood flow and also the time up to the arrival of the contrast agent and the time up to maximum fill. These parameters provide important information about the state of the supplying arteries. Precise mathematical formulae for the calculation are described for example in the cited article by Leif Østergaard.

According to a fourth variant the first and second image data sets each comprise a series from consecutively recorded 3D images. These can again be 3D images, which were generated by a rotational pass of a C-arm x-ray device. This means that the 3D images cannot currently be recorded with the same temporal resolution like the 2D images so a longer contrast agent bolus is preferably also injected here. It is also possible to generate a 3D image every two to three seconds. It is possible to calculate for example the BF, MTT etc. from the concentration pattern. The fourth variant can also be embodied like the third variant.

Each injection of contrast agent takes place shortly before each acquisition of a series or in the initial phase of the acquisition of a series of 2D images or 3D images.

Since the series of the first and second image data sets are generated with different contrast agent injections, normalization of the results obtained to the quantity of contrast agent and the injection profile is also expedient for the third and fourth variants. The quantitative evaluation of the perfusion parameters, such as BF, MTT, etc., depends on the bolus geometry; therefore normalization of the measured contrast concentration/time pattern in the tissue against AIF is expedient in this instance too. A region of interest (ROI) for example is selected by the user, which is preferably in the region of the supplying artery, into which the contrast agent is also injected. The time intensity curve in this ROI is taken as the AIF. However this ROI is preferably not selected automatically, for example in that the computation module takes the area with the earliest time to peak as the AIF. The normalized pattern over time of the contrast agent in the tissue is obtained for example by developing the measured contrast concentration/time pattern with the AIF, as described by Leif Østergaard in the above-mentioned article.

According to one embodiment therefore a normalized first and second image data set, in which the series of recorded images is developed pixel by pixel with the AIF, are first calculated from the first and second image data sets.

It is clear that with the first and third variants the functional data sets are two-dimensional, while the second and fourth variants allow three-dimensional functional data sets to be generated.

The linking of the first and second functional data sets according to the first method takes place for example by means of pixel-based addition or multiplication or the maximum of the two, with the first and/or second functional data set optionally being previously segmented and/or normalized, as described above. Segmentation can serve to set non-perfused regions, e.g. bones and air, to zero. It is also possible by this means to selected particularly interesting regions, e.g. a tumor, in a selective manner.

The linking of the first and second image data sets to form an overall image data set according to the second method preferably takes place by means of pixel-based addition or weighted addition, with the first and/or second image data set optionally being previously segmented and/or normalized. The images of the first and second image data sets are preferably registered with one another before they are linked or before the first and second functional data sets are generated.

Since slight movement of the patient cannot be excluded between the individual recordings of the 2D images or 3D images within a series, the 2D images and 3D images of a series are preferably registered with one another. This can be done based on the contrasted vessels.

If the 2D or 3D images were generated using a C-arm x-ray device, such calibration of the projection images will allow the theoretical position of any three-dimensional structure in space to be calculated on a projection image recorded with any settings (angulation, displacement of patient couch, etc.). In other words, if the position of a structure in the examination region is known, it can be calculated where this structure would be mapped on a projection image recorded from any projection direction. Such a registration method is described for example in US 2006/0285738 A1.

It is also possible to register the 2D or 3D images of different series with one another. This is particularly advantageous if time has passed between the acquisition of the individual series, e.g. due to displacement of the injection catheter into a different vessel, and the patient has moved in the meantime. It is also possible to compensate for displacement of the C-arm between the series by such a registration between the individual series. To register the different series with one another, the native images for example are again registered with one another in each instance. This is done for example by means of bony structures, which are present in the native images.

Alternatively the first and second functional data sets could also be registered with one another.

The first and second functional data sets are preferably generated by means of selective or superselective contrast agent injection into different arteries.

Selective contrast agent injection refers to an injection into a vessel supplying the perfused region, for example the left carotid artery (Arteria carotis communis), when a functional data set is to be calculated for the left hemisphere of the brain. Superselective contrast agent injection refers to an injection into a smaller vessel, in particular into one of a number of vessels, which supply a particular region, e.g. injection into a branch of the internal carotid artery (Arteria carotis interna).

Once the functional data sets or an overall functional data set have/has been generated, they are preferably displayed with color coding to facilitate analysis of the perfusion of the region under consideration. Such a color-coded display can be superimposed for example with a gray-scale display of a morphological image data set of the same region. This was recorded beforehand for example by means of CT, MRT or a C-arm x-ray device (by means of C-arm CT) and is registered with the first and second image data sets or the functional data sets, so that the perfusion data is displayed on the corresponding structures on the morphological images.

The inventive method also has the advantage that the collateral supply to certain regions can be assessed, being a significant prognostic factor for various disease patterns. By comparing a first and second functional data set it can be easily ascertained whether a certain region is supplied by a number of arteries and with what weighting. For the purposes of qualitative evaluation when linking a first and second functional data set it is possible to display for example two data sets in different colors and superimpose them. The area of mixed color is then supplied by both arteries.

A further object of the present invention is to specify an apparatus which is suitable for implementing the inventive method. The inventive apparatus comprises:

an image recording system for acquiring a first and second image data set, each comprising at least two images of a perfused region of the human or animal body, which were recorded at different times before and after an injection of contrast agent into an artery supplying the region;

a data storage unit for storing the first and second image data sets;

a computation module for generating functional data sets by means of pixel-based calculation of at least one perfusion parameter from the first and second image data sets or from an overall image data set, which was generated by linking from the first and second image data sets, and a screen to display the functional data sets.

The recording system is preferably an x-ray device, in particular an angiography device according to the above definition. It is preferably suitable for the acquisition of 2D images and 3D images by means of a rotational pass. The computation module is preferably designed to carry out the linking and analysis steps described above.

The apparatus also preferably comprises a control facility, which controls the image recording system accordingly so that the inventive method can be executed.

The apparatus can also have an injection facility for administering the contrast agent, it being possible for this to be controlled with a certain pattern over time, in particular for administering a contrast agent bolus.

A further object of the present invention is the improved provision of information relating to the form and scope of a flow of blood through tissue for medical staff. This object is achieved by using a method and/or an apparatus as claimed in one of the claims referred to above during a medical intervention. It is preferably possible during the intervention to use C-arm-based imaging for example to facilitate the definition of tissue acutely damaged by a stroke or infarction or adjacent tissue.

According to a further aspect of the invention it is also directed toward the use of an angiography device for generating functional data sets, which contain perfusion data of a region displayed in the functional data set. The perfusion data can be one of the perfusion parameters referred to above. These are determined by bolus tracking methods, in other words by evaluating at least two images, which were recorded at different times before and after an injection of contrast agent into a vessel supplying the region, in particular an artery.

BRIEF DESCRIPTION OF THE DRAWINGS

The invention is described in more detail below based on exemplary embodiments with reference to the accompanying drawings, in which.

DETAILED DESCRIPTION OF THE INVENTION

Figure 1:
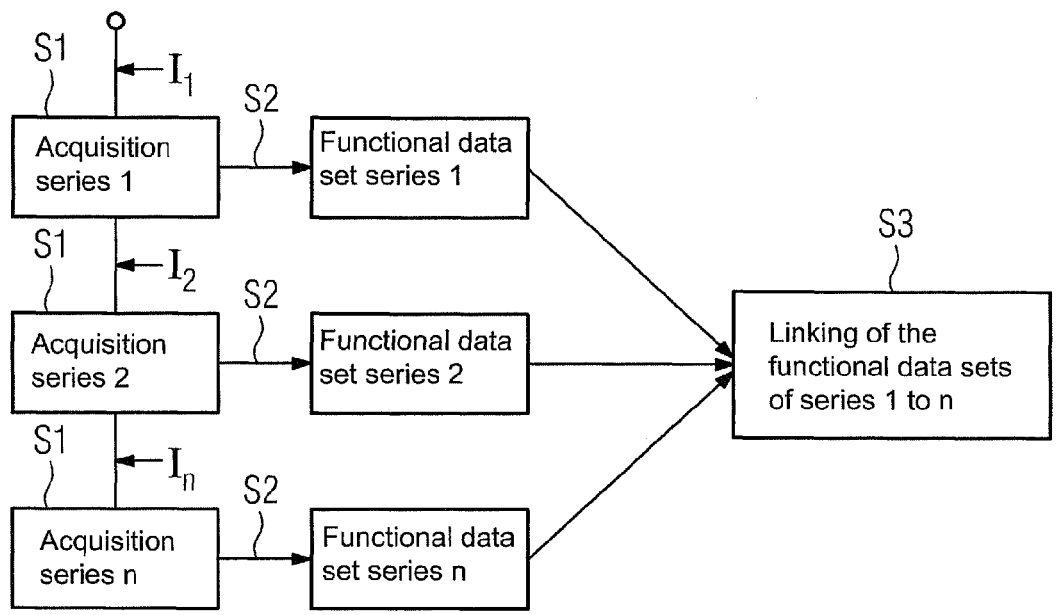
FIG. 1 shows a flow diagram of the inventive method.

FIG. 1 shows a flow diagram of the inventive method. The purpose of the inventive method is to obtain information about the overall resulting perfusion of perfused structures, such as the brain, liver, etc., based on a number of selective or superselective individual contrast agent injections ($I_1$ to $I_n$). n is a whole natural number and indicates the number of individual contrast agent injections and also the number of respective image data sets of the perfused region. Each image data set in this exemplary embodiment contains a series of consecutively recorded 2D or 3D images of the region. The method consists of a number of steps:

In a first step S1 a series of projection images of a region of the object is first respectively recorded (series 1 to n). This is done using any medical imaging method which is suitable for generating informative image recordings of the object of interest, e.g. the brain of a person or animal, with adequate temporal resolution to track a contrast agent bolus, e.g. projection radiography. The series of images can then be registered.

In a second step S2 the associated functional data set is extracted or calculated from each series of recorded images (series 1 to n). The data set can be a 2D or 3D data set— depending on the dimension of the recorded images.

In the last step S3 the respective functional data sets are linked to form an overall functional data set, to supply information about the overall perfusion of the perfused region or tissue or organ.

Figure 2:
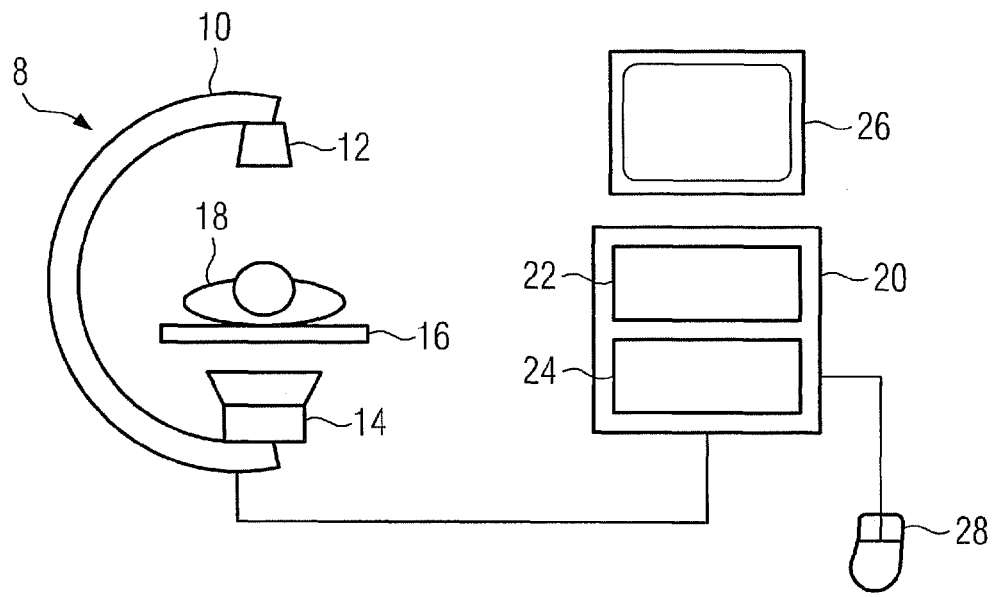
FIG. 2 shows a schematic diagram of an inventive apparatus.

FIG. 2 shows an exemplary embodiment of an apparatus that is suitable for executing the described method. It comprises an image recording system 8 with a C-arm 10, to the respective ends of which an x-ray tube 12 and an x-ray detector 14 are secured. The C-arm 10 can be moved freely about a patient couch 16, on which a patient 18 is supported. This allows projection images of the patient to be acquired from any projection directions.

These projection images are transferred to the data storage unit 22 of a control and image processing computer 20. The computer 20 also contains a computation module 24, which can be used to calculate functional data sets from the recorded projection images, these in turn forming the basis for calculating the overall functional data set of the organ.

Also attached to the control and image processing computer 20 are a screen 26 for displaying the projection images and functional data sets and a mouse 28 for selecting points, lines, regions, etc. on the projection images. Alternatively the means 28 can also be another cursor moving means such as a trackball or touchscreen.

Figure 3:
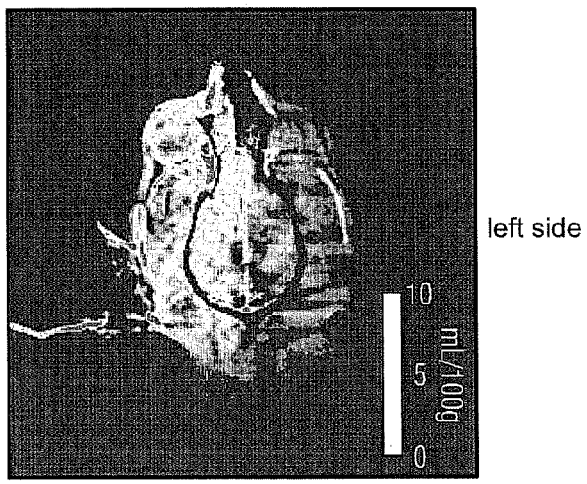
FIGS. 3 to 5 show diagrams of the blood volume of a brain by means of intra-arterial contrast agent injections.
Figure 4:
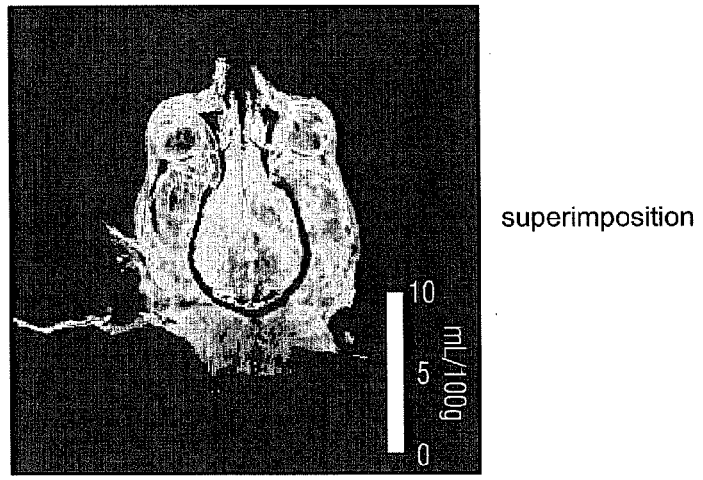
Figure 5:
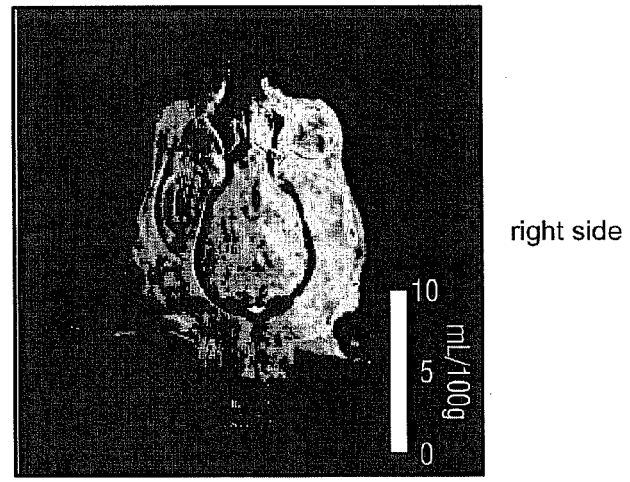

FIGS. 3 to 5 finally show images of the blood volume of a brain by means of intra-arterial contrast agent injections. FIG. 3 shows an image of the first functional data set, obtained by injecting contrast agent into the left internal carotid artery (Arteria carotis interna) and then acquiring a series of projection images of the brain. As can be clearly seen, the left hemisphere of the brain, in which the blood contains contrast agent, shows a considerably greater blood volume than the right hemisphere of the brain, in which the blood contains no contrast agent or small quantities of contrast agent due to the Circulus Willisi (Circulus arteriosus cerebri). FIG. 4 shows the image of the second functional data set, which was obtained by injecting contrast agent into the right internal carotid artery (Arteria carotis interna) and then acquiring a series of projection images of the brain. As can be clearly seen, here the right hemisphere of the brain, in which the blood contains contrast agent, shows a considerably greater blood volume than the left hemisphere of the brain, in which the blood contains no contrast agent or small quantities of contrast agent due to the Circulus arteriosus cerebri. FIG. 5 finally shows an image of the overall functional data set of the brain, obtained by superimposition (addition) of the first and second functional data sets from FIGS. 3 and 4.

Exemplary embodiments of the workflow during the application of the inventive method are described briefly below:

The instance of the first or second variant is described first, wherein the first and second image data sets consist relatively statically of just a few 2D or 3D images:

1. Acquisition of a native image.
2. Acquisition of a number of images shortly after the selective or superselective contrast agent injection into different arteries.
3. In the case of 3D images, reconstruction of the projection images recorded respectively during a rotational pass, to form a 3D image.
4. Functional analysis of the individual image data sets, for example calculation of CBV including AIF normalization.
5. Registration of the functional data sets calculated in step 4 based on the respective native images of the individual image data sets.
6. Linking of the functional data sets.
7. Analysis of the overall functional data set, e.g. segmentation for volume determination, overall blood volume, extent of collateral supply, etc.

For the functional analysis it is possible either to use the respective images at maximum fill with contrast agent or to subtract the native image from the maximum fill image beforehand. If subtracted data sets are used, it is possible to use just one shared native 3D image for subtraction to create all the functional data sets. In some instances a movement correction must be made or the data sets are registered correspondingly with one another.

The workflow in the third and fourth variants, in which a series of 2D or 3D images is respectively recorded, could be roughly as follows:

1. Acquisition of a number of series of temporally consecutive 2D or 3D images, with selective or superselective contrast agent injection into different arteries.
2. In some instances reconstruction of 3D images from rotational passes.
3. Generation of a time-coded representation for each image data set.
4. Nominalization of the different images based on the AIF.
5. Registration of the different images by means of the DSA information.
6. Linking of the different image data sets (2D or 3D) to form an overall image data set.

7. Analysis of the overall data set (calculation of the blood volume, blood flow, MTT, time of arrival, time to peak or other functional parameters).

8. Calculation of an overall functional data set.

The invention claimed is:

1. A method for generating a functional data set of a perfused region of a human or animal body, comprising:
   injecting an contrast agent into a first artery supplying the region;
   recording first two images of the perfused region at different times before and after the injection of the contrast agent into the first artery supplying the region using an angiography device;
   supplying a first image data set comprising the first two images using the angiography device;
   selecting a second artery supplying the region that is adjacent to and different from the first artery supplying the region;
   separately injecting the contrast agent into the second artery supplying the region;
   recording second two images of the perfused region at different times before and after the separate injection of the contrast agent into the second artery supplying the region using the angiography device;
   supplying a second image data set comprising the second two images using the angiography device;
   generating a first functional data set by pixel-based calculation of a first perfusion parameter from the first image data set using a computation device that measures the perfusion of the first artery supplying the region;
   generating a second functional data set by pixel-based calculation of a second perfusion parameter from the second image data set using the computation device that measures the perfusion of the second artery supplying the region; and
   displaying the first and the second functional data sets on a screen.

2. The method as claimed in claim 1, further comprising linking the first and the second functional data sets to form an overall functional data set.

3. The method as claimed in claim 1, wherein the first and the second image data sets each comprises a native 2D image and a contrasted 2D image.

4. The method as claimed in claim 1, wherein the first and the second image data sets each comprises a native 3D image and a contrasted 3D image recorded by a rotational pass of a C-arm x-ray device.

5. The method as claimed in claim 1, wherein the first and the second image data sets each comprises a series from consecutively recorded 2D images.

6. The method as claimed in claim 1, wherein the first and the second image data sets each comprises a series from consecutively recorded 3D images by a rotational pass of a C-arm x-ray device.

7. The method as claimed in claim 1,
   wherein the first and the second functional data sets are linked by a pixel-based addition, a pixel-based subtraction, or a pixel-based multiplication, and
   wherein the first or the second functional data set is previously segmented or normalized.

8. The method as claimed in claim 1, wherein the first and the second two images are registered with one another before linking or before the first and the second functional data sets are generated.

9. The method as claimed in claim 1, wherein the first and the second perfusion parameters are selected from the group consisting of: blood volume, blood flow, time to arrival of the contrast agent concentration, time to maximum fill, Mean Transit Time of the contrast agent, and a parameter proportional to one of values the above parameters.

10. The method as claimed in claim 1, wherein the first and the second functional data sets are superimposed with a morphological image data set of the perfused region for evaluation.

11. A method for generating at least one functional data set of a perfused region of a human or animal body, comprising:
    injecting an contrast agent into a first artery supplying the region;
    recording first two images of the perfused region at different times before and after the injection of the contrast agent into the first artery supplying the region using an angiography device;
    supplying a first image data set comprising the first two images using the angiography device that measures the perfusion of the first artery supplying the region;
    selecting a second artery supplying the region that is adjacent to and different from the first artery supplying the region;
    separately injecting the contrast agent into a second artery supplying the region;
    recording second two images of the perfused region at different times before and after the injection of the contrast agent into the second artery supplying the region using the angiography device;
    supplying a second image data set comprising the second two images using the angiography device that measures the perfusion of the second artery supplying the region;
    linking the first and the second image data sets to form an overall image data set using a computation device;
    generating an overall functional data set by pixel-based calculation of a perfusion parameter from the overall image data set using the computation device; and
    displaying the overall functional data set on a screen.

12. The method as claimed in claim 11,
    wherein the first and the second image data sets are linked by a pixel-based addition, and
    wherein the first or the second image data set is previously segmented or normalized.

13. The method as claimed in claim 11, wherein the overall functional data set is superimposed with a morphological image data set of the perfused region for evaluation.

14. An apparatus generating at least one functional data set of a perfused region of a human or animal body, comprising:
    an image recording system for:
      injecting an contrast agent into a first artery supplying the region;
      recording first two images of the perfused region at different times before and after the injection of the contrast agent into the first artery supplying the region;
      supplying a first image data set comprising the first two images that measures the perfusion of the first artery supplying the region;
      selecting a second artery supplying the region that is adjacent to and different from the first artery supplying the region;
      separately injecting the contrast agent into a second artery supplying the region;
      recording second two images of the perfused region at different times before and after the injection of the contrast agent into the second artery supplying the region; and supplying a second image data set comprising the second two images that measures the perfusion of the second artery supplying the region;

a data storage unit for storing the first and the second image data sets;

a computation device for generating functional data sets by pixel-based calculation of a perfusion parameter from the first and the second image data sets; and a screen for displaying the functional data sets.

15. The apparatus as claimed in claim 14, wherein the functional data sets are generated from the first and the second image data sets respectively or from an overall image data set by linking the first and the second image data sets.

16. The apparatus as claimed in claim 14, wherein the image recording system is an x-ray device comprising an x-ray tube and an x-ray detector which can be moved around the perfused region.

* * * * *